United States Patent
Sonderman et al.

(10) Patent No.: US 7,117,062 B1
(45) Date of Patent: Oct. 3, 2006

(54) DETERMINING TRANSMISSION OF ERROR EFFECTS FOR IMPROVING PARAMETRIC PERFORMANCE

(75) Inventors: Thomas J. Sonderman, Austin, TX (US); Robert J. Chong, Austin, TX (US); Brian K. Cusson, Austin, TX (US); Alexander J. Pasadyn, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 441 days.

(21) Appl. No.: 10/323,553

(22) Filed: Dec. 18, 2002

(51) Int. Cl.
*G06F 19/00* (2006.01)

(52) U.S. Cl. .................. 700/121; 700/109; 714/51; 427/10

(58) Field of Classification Search ............. 700/121, 700/108–110, 105, 117, 17, 29–34, 83, 51, 700/37, 38, 39, 45, 104; 714/51; 716/19; 702/84; 427/10
See application file for complete search history.

(56) References Cited

U.S. PATENT DOCUMENTS

| | | | | |
|---|---|---|---|---|
| 5,661,669 A | * | 8/1997 | Mozumder et al. | 702/84 |
| 5,801,965 A | * | 9/1998 | Takagi et al. | 702/35 |
| 6,522,939 B1 | * | 2/2003 | Strauch et al. | 700/116 |

* cited by examiner

*Primary Examiner*—Kidest Bahta
(74) *Attorney, Agent, or Firm*—Williams, Morgan & Amerson, P.C.

(57) ABSTRACT

A method and an apparatus for characterizing an uncertainty factor relating to processing workpieces. A first processing step is performed upon a workpiece. A first uncertainty factor associated with the first processing step is calculated. A final uncertainty factor associated with an end-of-line parameter relating to the workpiece is calculated based upon the first uncertainty factor. A process control function based upon the final uncertainty factor is performed.

33 Claims, 8 Drawing Sheets

DETERMINING TRANSMISSION OF ERROR EFFECTS FOR IMPROVING PARAMETRIC PERFORMANCE

BACKGROUND OF THE INVENTION

1. Field of the Invention

This invention relates generally to semiconductor manufacturing, and, more particularly, to a method and apparatus for improving performance of one or more parameters relating to a wafer process based upon error effects that transmit throughout a manufacturing system.

2. Description of the Related Art

The technology explosion in the manufacturing industry has resulted in many new and innovative manufacturing processes. Today's manufacturing processes, particularly semiconductor manufacturing processes, call for a large number of important steps. These process steps are usually vital, and therefore, require a number of inputs that are generally fine-tuned to maintain proper manufacturing control.

The manufacture of semiconductor devices requires a number of discrete process steps to create a packaged semiconductor device from raw semiconductor material. The various processes, from the initial growth of the semiconductor material, the slicing of the semiconductor crystal into individual wafers, the fabrication stages (etching, doping, ion implanting, or the like), to the packaging and final testing of the completed device, are so different from one another and specialized that the processes may be performed in different manufacturing locations that contain different control schemes.

Generally, a set of processing steps is performed across a group of semiconductor wafers, sometimes referred to as a lot. For example, a process layer that may be composed of a variety of different materials may be formed across a semiconductor wafer. Thereafter, a patterned layer of photoresist may be formed across the process layer using known photolithography techniques. Typically, an etch process is then performed across the process layer using the patterned layer of photoresist as a mask. This etching process results in the formation of various features or objects in the process layer. Such features may be used as, for example, a gate electrode structure for transistors. Many times, trench isolation structures are also formed across the substrate of the semiconductor wafer to isolate electrical areas across a semiconductor wafer. One example of an isolation structure that can be used is a shallow trench isolation (STI) structure.

The manufacturing tools within a semiconductor manufacturing facility typically communicate with a manufacturing framework or a network of processing modules. Each manufacturing tool is generally connected to an equipment interface. The equipment interface is connected to a machine interface to which a manufacturing network is connected, thereby facilitating communications between the manufacturing tool and the manufacturing framework. The machine interface can generally be part of an advanced process control (APC) system. The APC system initiates a control script, which can be a software program that automatically retrieves the data needed to execute a manufacturing process.

FIG. 1 illustrates a typical semiconductor wafer 105. The semiconductor wafer 105 typically includes a plurality of individual semiconductor die 103 arranged in a grid 150. Using known photolithography processes and equipment, a patterned layer of photoresist may be formed across one or more process layers that are to be patterned. As part of the photolithography process, an exposure process is typically performed by a stepper on approximately one to four die 103 locations at a time, depending on the specific photomask employed. The patterned photoresist layer can be used as a mask during etching processes, wet or dry, performed on the underlying layer or layers of material, e.g., a layer of polysilicon, metal or insulating material, to transfer the desired pattern to the underlying layer. The patterned layer of photoresist is comprised of a plurality of features, e.g., line-type features or opening-type features that are to be replicated in an underlying process layer.

Turning now to FIG. 2, a typical flow of processes performed on a semiconductor wafer 105 by a semiconductor manufacturing system is illustrated. A manufacturing system processes semiconductor wafers 105 by initiating a sequence of processes that are to be performed on a batch of semiconductor wafers 105 (block 210). The manufacturing system may then acquire and analyze metrology data relating to the processed semiconductor wafers 105 (blocks 220, 230).

Based on the analysis of the metrology data, the manufacturing system may determine whether there are further process steps to be performed on the semiconductor wafers 105 (block 240). Upon a determination that there are no further process steps to be performed on the semiconductor wafers 105, the manufacturing system stops processing the wafers 105 (block 250). Upon a determination that additional process steps are to be performed on the wafers 105, the manufacturing system may calculate adjustments to be made to the subsequent process based upon the metrology data analysis (block 260). The manufacturing system then performs the modified process to correct or compensate for errors discovered during the analysis of the metrology data (block 270).

Among the problems associated with the current methodology include the fact that there may be a finite amount of uncertainty relating to the accuracy of one or more process steps that are performed on the wafers 105. Often, these uncertainties can accumulate, causing a cumulative error factor on the processed wafers 105. Additionally, these uncertainties in the process steps may cause an uncertainty in the finished wafers 105. Therefore, one or more end-of-line parameter(s) may have an inherent amount of uncertainty, thereby reducing confidence that the devices manufactured from the processed wafers 105 will operate properly.

Additionally, due to the uncertainty that may exist in certain processes, along with the uncertainty of the end-of-line parameters, controlling the process through modeling is more difficult. Therefore, the uncertainty relating to various portions of the manufacturing system may result in processed semiconductor wafers 105 of reduced quality.

The present invention is directed to overcoming, or at least reducing, the effects of, one or more of the problems set forth above.

SUMMARY OF THE INVENTION

In one aspect of the present invention, a method is provided for characterizing an uncertainty factor relating to processing workpieces. A first processing step is performed upon a workpiece. A first uncertainty factor associated with the first processing step is calculated. A final uncertainty factor associated with an end-of-line parameter relating to the workpiece is calculated based upon the first uncertainty factor. A process control function based upon the final uncertainty factor is performed.

In another aspect of the present invention, a method is provided for characterizing an uncertainty factor relating to processing workpieces. A first processing step is performed upon a workpiece. A first uncertainty factor associated with the first processing step is calculated. A second processing step is performed upon a workpiece. A second uncertainty factor associated with the second processing step is calculated. A final uncertainty factor associated with an end-of-line parameter relating to the workpiece is calculated based upon the first and second uncertainty factors. A process control function based upon the final uncertainty factor is performed.

In another aspect of the present invention, a system is provided for characterizing an uncertainty factor relating to processing workpieces. The system includes a first and a second processing tool to perform a first and second process upon a workpiece. The system also includes a controller operatively coupled to the first and second processing tools, the controller is adapted to determine a first uncertainty factor associated with the first processing step, determine a second uncertainty factor associated with the second processing step, determine a final uncertainty factor associated with an end-of-line parameter relating to the workpiece based upon the first and second uncertainty factors, and perform a process control function based upon the final uncertainty factor.

In another aspect of the present invention, an apparatus is provided for characterizing an uncertainty factor relating to processing workpieces. The apparatus includes a controller adapted to determine a first uncertainty factor associated with a first processing step performed on a workpiece. The controller is adapted to determine a second uncertainty factor associated with a second processing step performed on the workpiece, determine a final uncertainty factor associated with an end-of-line parameter relating to the workpiece based upon the first and second uncertainty factors, and perform a process control function based upon the final uncertainty factor.

In yet another aspect of the present invention, a computer readable program storage device encoded with instructions is provided for characterizing an uncertainty factor relating to processing workpieces. The computer readable program storage device encoded with instructions that, when executed by a computer, performs a method, which comprises: performing a first processing step upon a workpiece; determining a first uncertainty factor associated with the first processing step; determining a final uncertainty factor associated with an end-of-line parameter relating to the workpiece based upon the first uncertainty factor; and performing a process control function based upon the final uncertainty factor.

BRIEF DESCRIPTION OF THE DRAWINGS

The invention may be understood by reference to the following description taken in conjunction with the accompanying drawings, in which like reference numerals identify like elements, and in which.

Figure 1:
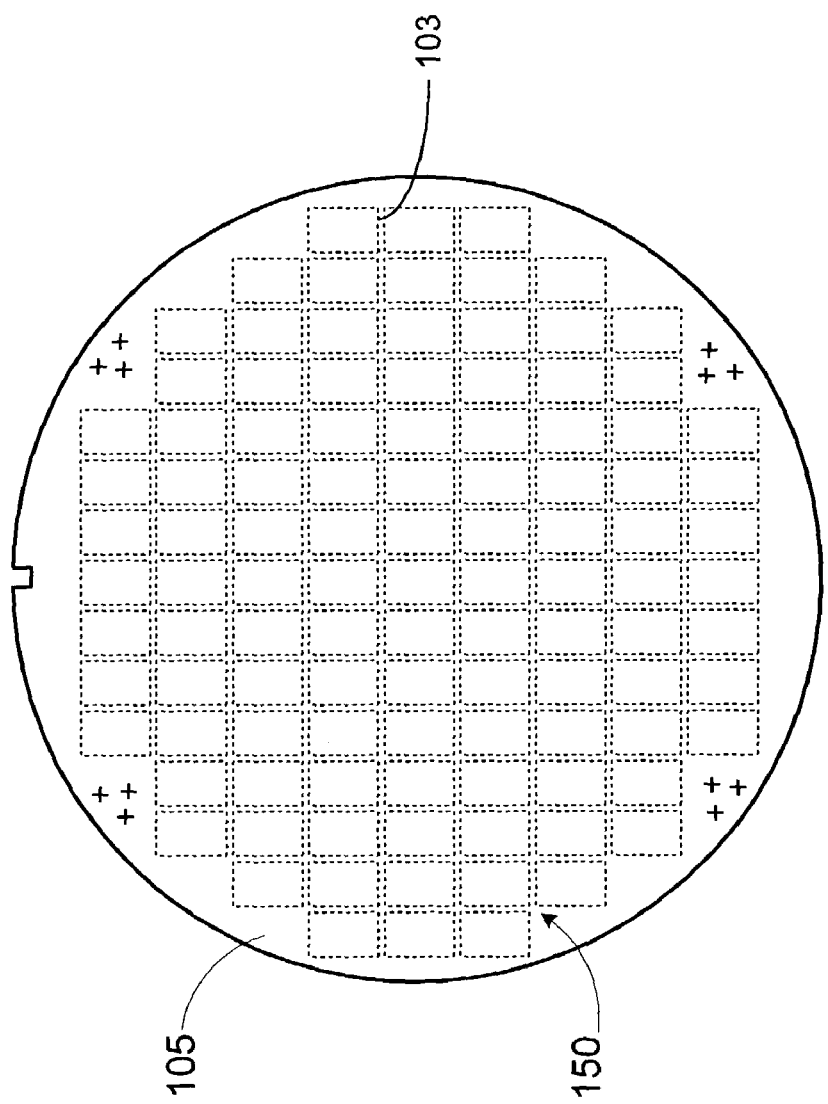
FIG. 1 is a simplified diagram of a prior art semiconductor wafer being processed.
Figure 2:
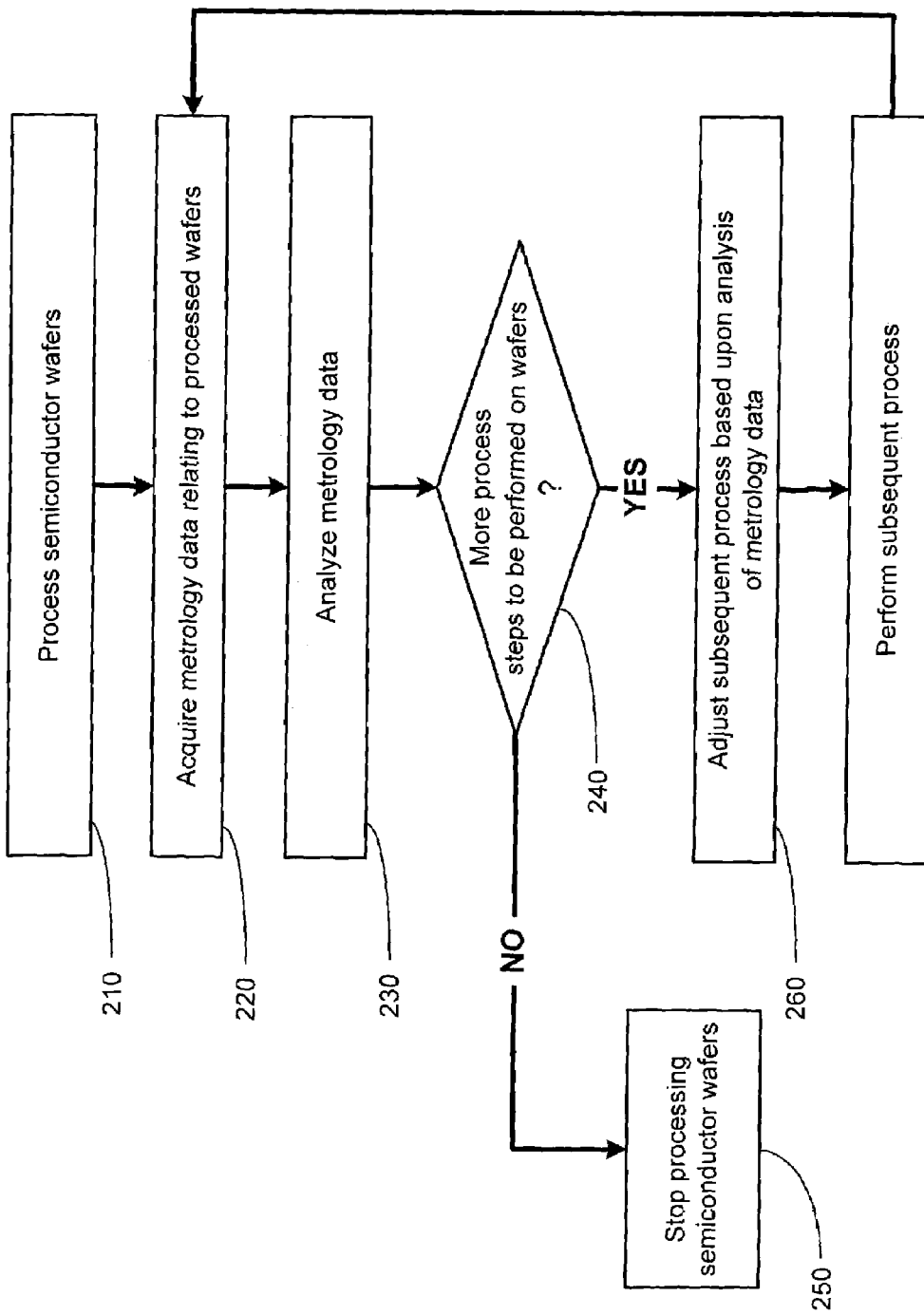
FIG. 2 illustrates a simplified flowchart depiction of a prior art process flow during manufacturing of semiconductor wafers.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involved in semiconductor manufacturing. Many times, workpieces (e.g., semiconductor wafers 105, semiconductor devices, etc.) are stepped through multiple manufacturing process tools. Embodiments of the present invention provide for characterizing an uncertainty factor, which may include an uncertainty of the accuracy of a process operation, relating to operations performed on semiconductor wafers 105. The uncertainty factor may be tracked throughout a manufacturing system. Therefore, an analysis of the accumulation of uncertainties in various processes and/or uncertainties in metrology measurements may be tracked to characterize an overall uncertainty relating to the processed semiconductor wafers 105.

Often, a plurality of unit operations or processes are performed on semiconductor wafers 105 as they are moved through various processing points of a manufacturing system. Each unit operation may contain an amount of uncertainty that may be characterized. Based upon this characterization, several uncertainty factors may be defined to characterize the various uncertainties of the processing wafers 105. Additionally, embodiments of the present invention may be used to characterize a final uncertainty factor based upon the uncertainty factors relating to the individual unit operations. Therefore, embodiments of the present invention may be used to characterize an end-of-line (EOL) parameter, such as a drive current, by characterizing the final uncertainty based upon a function that utilizes the individual uncertainties corresponding to various unit operations.

Figure 3:
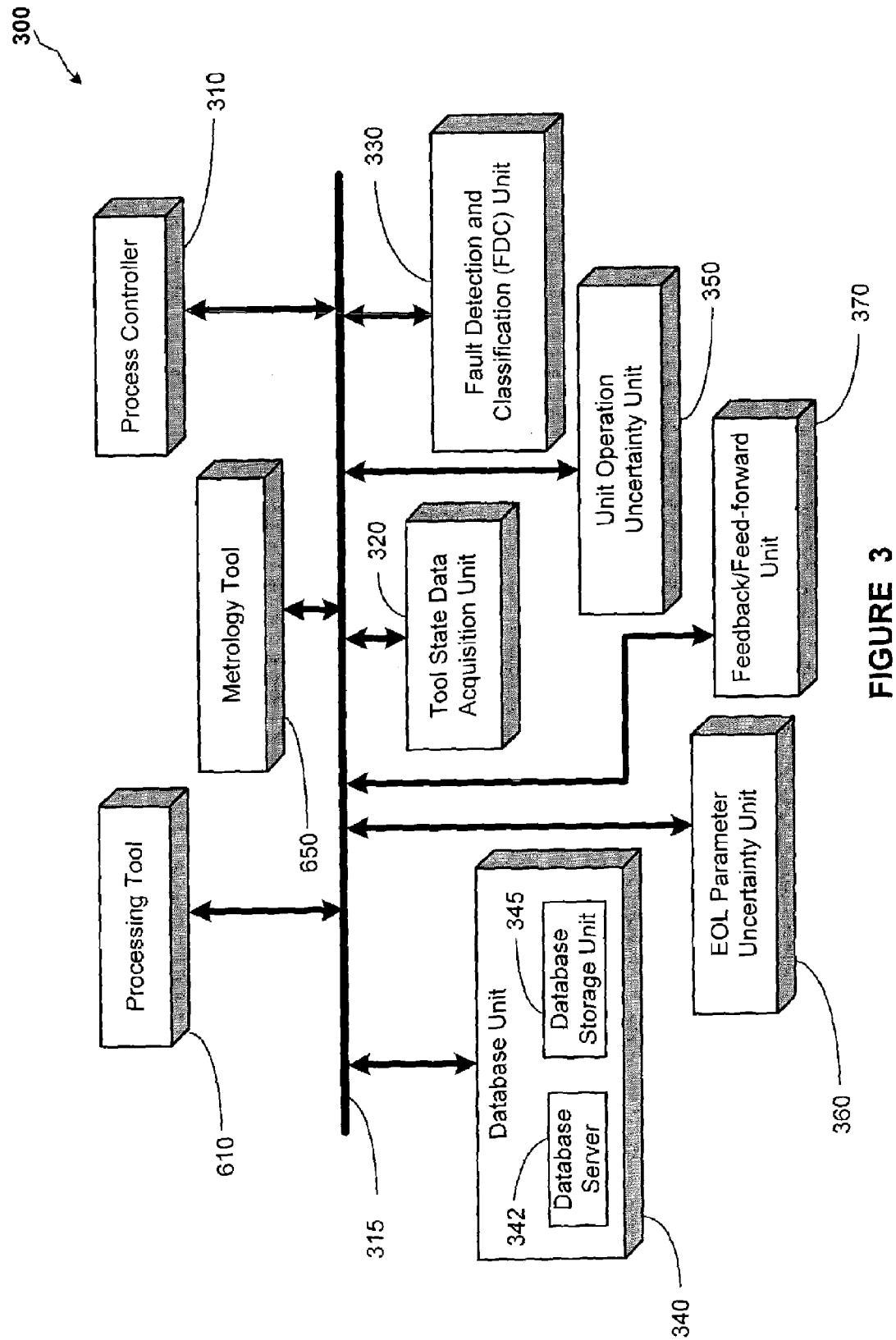
FIG. 3 provides a block diagram representation of a system in accordance with one illustrative embodiment of the present invention.

Turning now to FIG. 3, a block diagram depicting a system 300 in accordance with embodiments of the present invention is illustrated. A process controller 310 in the system 300 is capable of controlling various operations relating to a processing tool 610. The system 300 is capable of acquiring manufacturing related data, such as metrology data related to processed semiconductor wafers 105, tool state data, and the like. The system 300 may comprise a metrology tool 650 to acquire metrology data related to the processed semiconductor wafers 105.

The system 300 may also comprise a database unit 340. The database unit 340 is provided for storing a plurality of types of data, such as manufacturing-related data, data related to the operation of the system 300 (e.g., the status of the processing tool 610, the status of semiconductor wafers 105, etc.), and the like. The database unit 340 may store tool state data, such as tool state data relating to a plurality of process runs performed by the processing tool 610. The database unit 340 may comprise a database server 342 for storing tool state data and/or other manufacturing data related to processing semiconductor wafers 105 into a database storage unit 345.

The system 300 may also comprise a tool state data acquisition unit 320 for acquiring tool state data. The tool state data may include pressure data, temperature data, humidity data, gas flow data, various electrical data, and the like, related to operations of the processing tool 610. Exemplary tool state data for an etch tool may include gas flow, chamber pressure, chamber temperature, voltage, reflected power, backside helium pressure, RF tuning parameters, etc., that are traced and/or recorded throughout a period of time. Tool state data may also include data external to the processing tool 610, such as ambient temperature, humidity, pressure, etc. A more detailed illustration of the tool state data acquisition unit 320 is provided in FIG. 4 and accompanying description below.

The system 300 also comprises a fault detection and classification unit (FDC) 330 capable of performing various fault detection analyses relating to the processing of semiconductor wafers 105. The fault detection and classification unit 330 is capable of providing data relating to faults that occur while processing a semiconductor wafer 105. Fault detection analysis performed by the fault detection and classification unit 330 may include analysis of tool state data and/or metrology data. The FDC unit 330 may correlate particular tool state data to errors detected on the processed semiconductor wafer 105 by analyzing the metrology tool data. For example, particular errors, such as critical dimension errors discovered on the processed semiconductor wafers 105 may be correlated to particular gas flow rates or temperature data relating to tool state data. The fault detection performed by the FDC unit 330 may also include analyzing data from in situ sensors integrated into the processing tools 710.

The system 300 may also comprise an uncertainty unit 350 that is capable of characterizing an uncertainty factor ($\sigma_i$) relating to a unit operation. The uncertainty factor may include a characterization of the uncertainty relating to the accuracy of operation of a processing tool 610. The uncertainty unit 350 may characterize an uncertainty of particular unit operations, such as an implant operation, an operation to form a gate structure, a rapid thermal anneal (RTA) process, an etch process, and the like. During the processing of a batch of semiconductor wafers 105, several unit operations are performed on the wafers 105, therefore, several uncertainty factors may be defined (e.g., $\sigma_0$, $\sigma_1$, $\sigma_2$, . . . $\sigma_i$, . . . $\sigma_N$).

The system 300 also comprises an end-of-line (EOL) parameter uncertainty unit 360 (or EOL uncertainty unit 360). The EOL uncertainty unit 360 is capable of characterizing an uncertainty factor relating to one or more EOL parameters, such as the drive current. The EOL uncertainty unit 360 calculates the final uncertainty factor ($\sigma_F$) as a function of the various uncertainty factors relating to various unit operations performed on the wafers 105 (see Equation 1).

$$\sigma_F = f(\sigma_1, \sigma_2, \sigma_3, \ldots \sigma_N) \quad \text{Equation 1}$$

The EOL uncertainty unit 360 quantifies the aggregate uncertainty of the processes and predicts how such uncertainty can be used for calculating corrections during the processing of the semiconductor wafers 105. A feedback/feed-forward unit 370 may utilize data from the EOL uncertainty unit 360 and/or other manufacturing data to perform feedback corrections and/or feed-forward compensation for correcting errors on the semiconductor wafers 105.

The process controller 310, the FDC unit 330, the uncertainty unit 350, the EOL uncertainty unit 360, and/or the feedback/feed-forward unit 370 may be software, hardware, or firmware units that are standalone units or may be integrated into a computer system associated with the system 300. Furthermore, the various components represented by the blocks illustrated in FIG. 3 may communicate with one another via a system communications line 315. The system communications line 315 may be a computer bus link, a dedicated hardware communications link, a telephone system communications link, a wireless communications link, or other communication links that may be implemented by those skilled in the art having benefit of the present disclosure.

Figure 4:
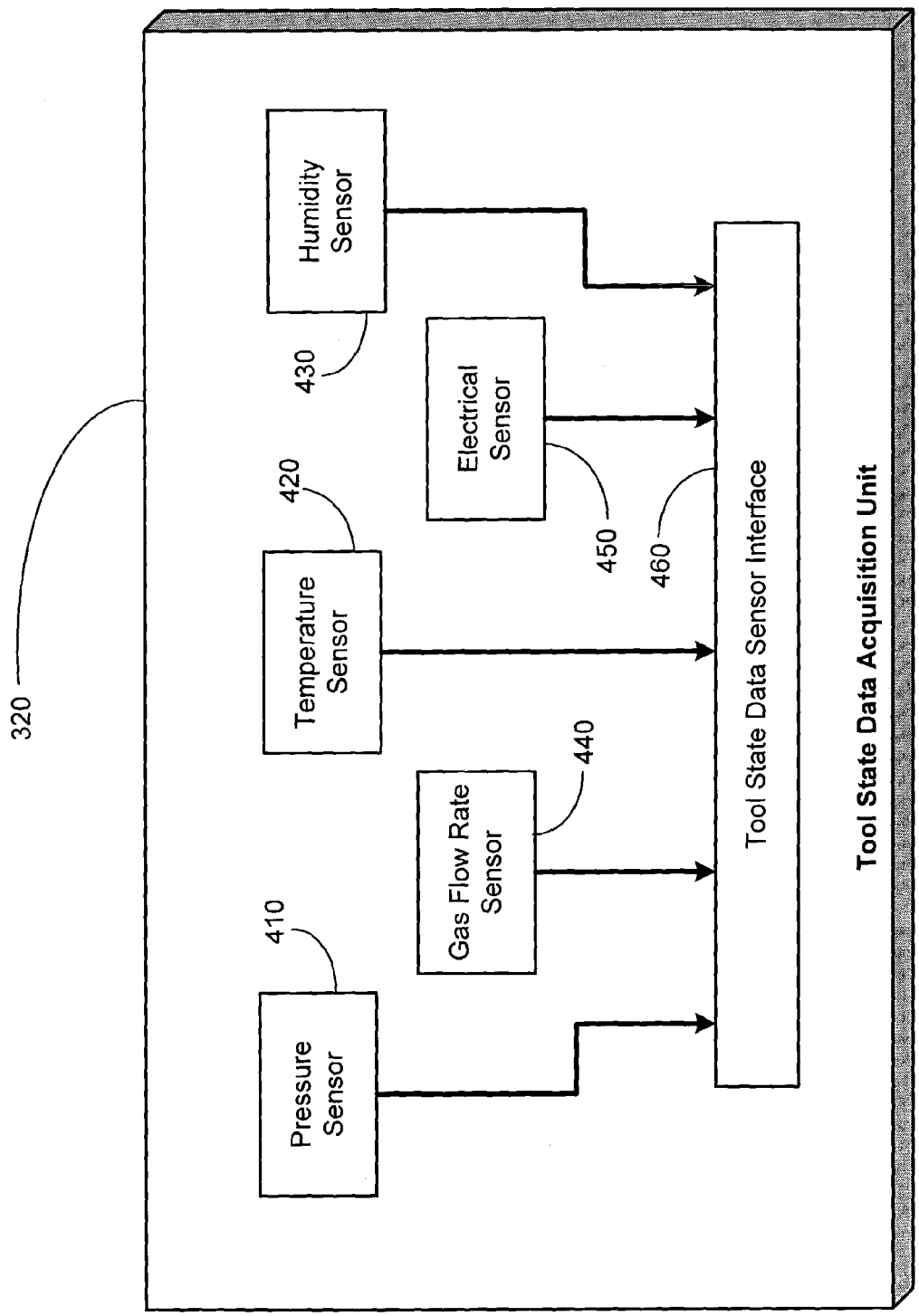
FIG. 4 illustrates a more detailed block diagram representation of a tool state data acquisition unit of FIG. 3, in accordance with one illustrative embodiment of the present invention.

Turning now to FIG. 4, a more detailed block diagram depicting the tool state data acquisition unit 320 illustrated in FIG. 3 is provided. The tool state data acquisition unit 320 may comprise any of a variety of different types of sensors, e.g., a pressure sensor 410, a temperature sensor 420, a humidity sensor 430, a gas flow rate sensor 440, an electrical sensor 450, etc. In an alternative embodiment, the tool state data acquisition unit 320 may comprise in situ sensors that are integrated into the processing tool 610. The pressure sensor 410 is capable of detecting the pressure within the processing tool 610. The temperature sensor 420 is capable of sensing the temperature of various portions of the processing tool 610. The humidity sensor 430 is capable of detecting the relative humidity at various portions in the processing tool 610, or of the surrounding ambient conditions. The gas flow rate sensor 440 may comprise a plurality of flow-rate sensors that are capable of detecting the flow-rate of a plurality of process gases utilized during processing of semiconductor wafers 105. For example, the gas flow rate sensor 440 may comprise sensors that can detect the flow rate of gases such as $NH_3$, $SiH_4$, $N_2$, $N_2O$, and/or other process gases.

In one embodiment, the electrical sensor 450 is capable of detecting a plurality of electrical parameters, such as the current provided to a lamp used in a photolithography process. The tool state data acquisition unit 320 may also comprise other sensors capable of detecting a variety of manufacturing variables known to those skilled in the art having benefit of the present disclosure. The tool state data acquisition unit 320 may also comprise an interface 460. The interface 460 may receive data from the various sensors that are contained within or associated with, the processing tool 610 and/or the tool state data acquisition unit 320 and transmit the data to the process controller 310.

Figure 5:
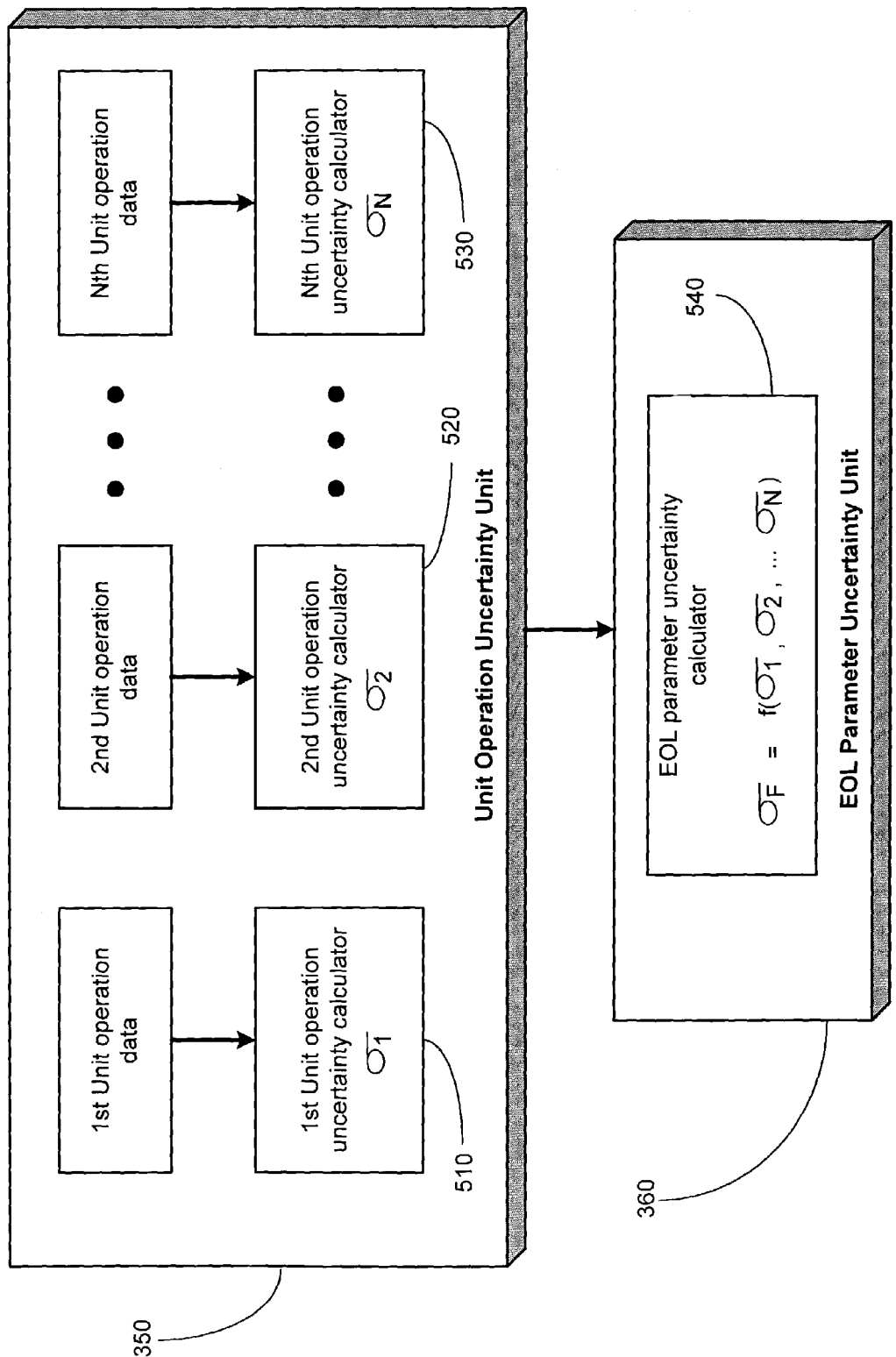
FIG. 5 illustrates a more detailed block diagram representation of a unit operation uncertainty unit and an EOL parameter uncertainty unit of FIG. 3, in accordance with one illustrative embodiment of the present invention.

Turning now to FIG. 5, a more detailed block diagram depicting the uncertainty unit 350 and the EOL uncertainty unit 360 are illustrated. The uncertainty unit 350 may comprise a $1^{st}$ through $N^{th}$ uncertainty calculator 510–530. These uncertainty calculators 510–530 correspond to a $1^{st}$ through $N^{th}$ unit operation that is performed on the wafers 105. Determining the uncertainty may also be viewed as determining a "certainty quantity" relating to a unit operation. The $1^{st}$ uncertainty calculator 510 receives data relating to the $1^{st}$ unit operation, and the $N^{th}$ uncertainty calculator 530 receives data from the $N^{th}$ unit operation performed on the wafers 105.

The $1^{st}$ unit operation may be a process that forms a gate of a transistor on a semiconductor wafer 105. The $1^{st}$ unit operation data may include critical dimensions relating to the gate. The $2^{nd}$ unit operation may be an implant process from which data relating to the implant process is sent to the $2^{nd}$ unit operation calculator 520. The $N^{th}$ unit operation data may be an etching process that sends measurement data of structures subsequent to an etch process to the $N^{th}$ uncertainty calculator 530. The uncertainty unit 350 may also receive tool state data from various processing tools 610 that perform the unit operations.

Using the received data, the uncertainty calculators 510–530 generate a plurality of uncertainty factors relating to individual unit operations ($\sigma_1, \sigma_2 \ldots \sigma_N$). The uncertainty factors ($\sigma_1, \sigma_2 \ldots \sigma_N$) are received by the EOL parameter uncertainty unit 360, which may comprise an EOL uncertainty calculator 540. The EOL uncertainty calculator 540 may calculate a final uncertainty factor relating to a particular EOL parameter based upon a function that utilizes the unit operation uncertainty factors (see Equation 1). For example, the EOL uncertainty calculator 540 may characterize the uncertainty factor for a drive current, a saturation current, a break-through voltage, a ring oscillation, an operating speed, and the like, and define the uncertainty relating to the accuracy of the EOL parameter. The system 300 may then utilize the uncertainty factors relating to the EOL parameters to make adjustments to the process operations.

Figure 6:
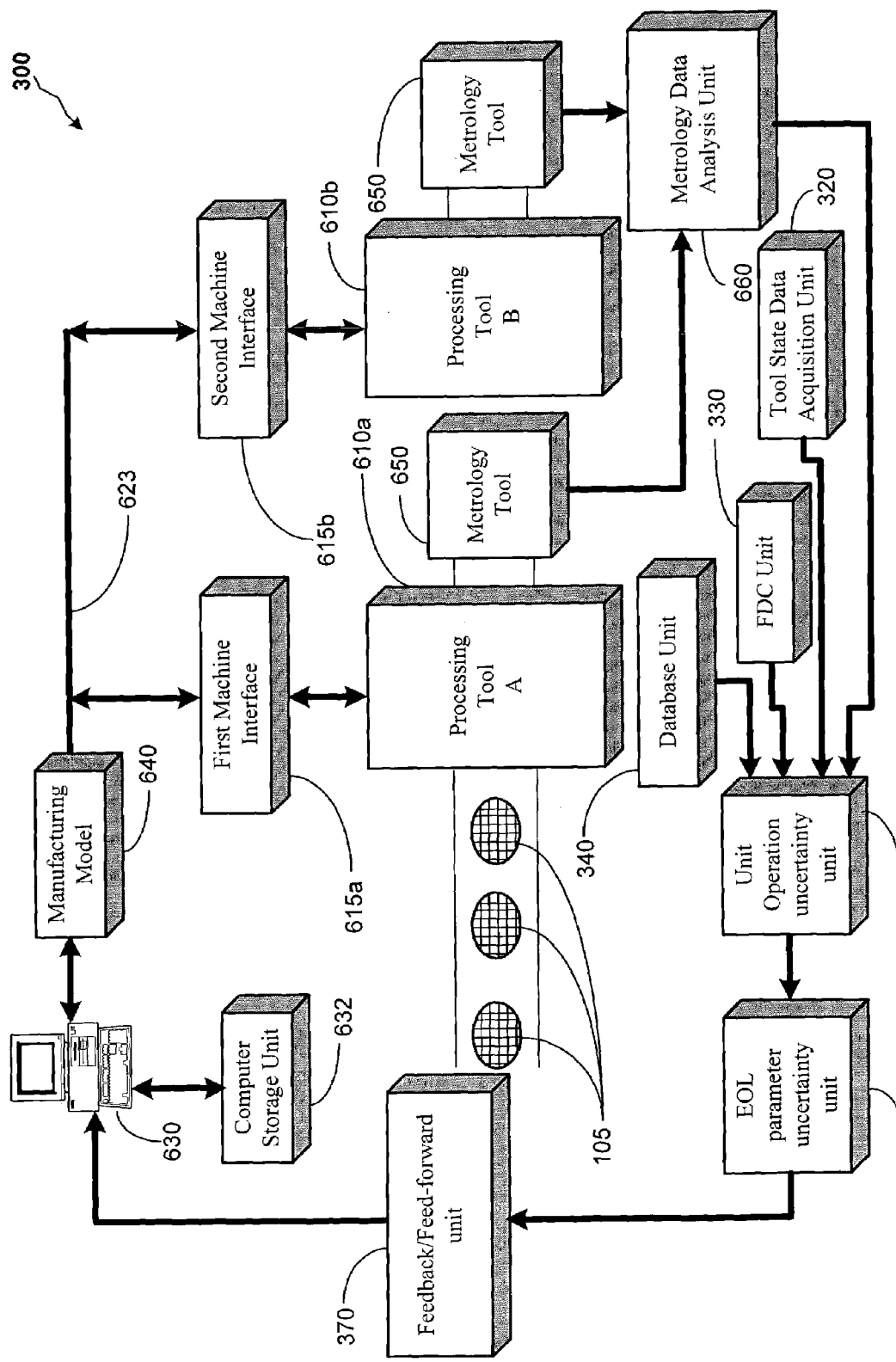
FIG. 6 illustrates a more detailed block diagram representation of the system shown in FIG. 3, in accordance with one illustrative embodiment of the present invention.

Turning now to FIG. 6, a more detailed block diagram of the system 300 in accordance with one embodiment of the present invention is illustrated. Semiconductor wafers 105 are processed on processing tools 610a, 610b using a plurality of control input signals, or manufacturing parameters, provided via a line or network 623. The control input signals, or manufacturing parameters, on the line 623 are sent to the processing tools 610a, 610b from a computer system 630 via machine interfaces 615a, 615b. The first and second machine interfaces 615a, 615b are generally located external the processing tools 610a, 610b. In an alternative embodiment, the first and second machine interfaces 615a, 615b are located within the processing tools 610a, 610b. The semiconductor wafers 105 are provided to and carried from a plurality of processing tools 610. In one embodiment, semiconductor wafers 105 may be provided to a processing tool 610 manually. In an alternative embodiment, semiconductor wafers 105 may be provided to a processing tool 610 in an automatic fashion (e.g., robotic movement of semiconductor wafers 105). In one embodiment, a plurality of semiconductor wafers 105 is transported in lots (e.g., stacked in cassettes) to the processing tools 610.

In one embodiment, the computer system 630 sends control input signals, or manufacturing parameters, on the line 623 to the first and second machine interfaces 615a, 615b. The computer system 630 is capable of controlling processing operations. In one embodiment, the computer system 630 is a process controller. The computer system 630 is coupled to a computer storage unit 632 that may contain a plurality of software programs and data sets. The computer system 630 may contain one or more processors (not shown) that are capable of performing the operations described herein. The computer system 630 employs a manufacturing model 640 to generate control input signals on the line 623. In one embodiment, the manufacturing model 640 contains a manufacturing recipe that determines a plurality of control input parameters that are sent on the line 623 to the processing tools 610a, 610b.

In one embodiment, the manufacturing model 640 defines a process script and input control that implement a particular manufacturing process. The control input signals (or control input parameters) on the line 623 that are intended for processing tool A 610a are received and processed by the first machine interface 615a. The control input signals on the line 623 that are intended for processing tool B 610b are received and processed by the second machine interface 615b. Examples of the processing tools 610a, 610b used in semiconductor manufacturing processes are steppers, etch process tools, deposition tools, and the like.

One or more of the semiconductor wafers 105 that are processed by the processing tools 610a, 610b can also be sent to a metrology tool 650 for acquisition of metrology data. The metrology tool 650 may be a scatterometry data acquisition tool, an overlay-error measurement tool, a critical dimension measurement tool, and the like. In one embodiment, a metrology tool 650 examines one or more processed semiconductor wafers 105. The metrology data analysis unit 660 may collect, organize, and analyze data from the metrology tool 650. The metrology data is directed to a variety of physical or electrical characteristics of the devices formed across the semiconductor wafers 105. For example, metrology data may be obtained as to line width measurements, depth of trenches, sidewall angles, thickness, resistance, and the like. Metrology data may be used to determine faults that may be present across the processed semiconductor wafers 105, which may be used to quantify the performance of the processing tools 610.

As provided above, the unit operation uncertainty unit 350 may receive unit operation data from the database unit 340, the FDC unit 330, the tool state data unit 320, and/or the metrology data analysis unit 660. Utilizing data relating to the processing tools 610 and the process operations performed on the semiconductor wafers 105, the unit operation uncertainty unit 350 provides data to the EOL uncertainty unit 360 for calculating uncertainty factors relating to one or more EOL parameters. Using the uncertainty factors of the EOL parameters, the system 300 may perform a feedback/feed-forward correction as provided by the feedback/feed-forward unit 370. Utilizing the uncertainty factors, further adjustments to feedback/feed-forward process controls may be made for more accurate processing of semiconductor wafers 105.

Figure 7:
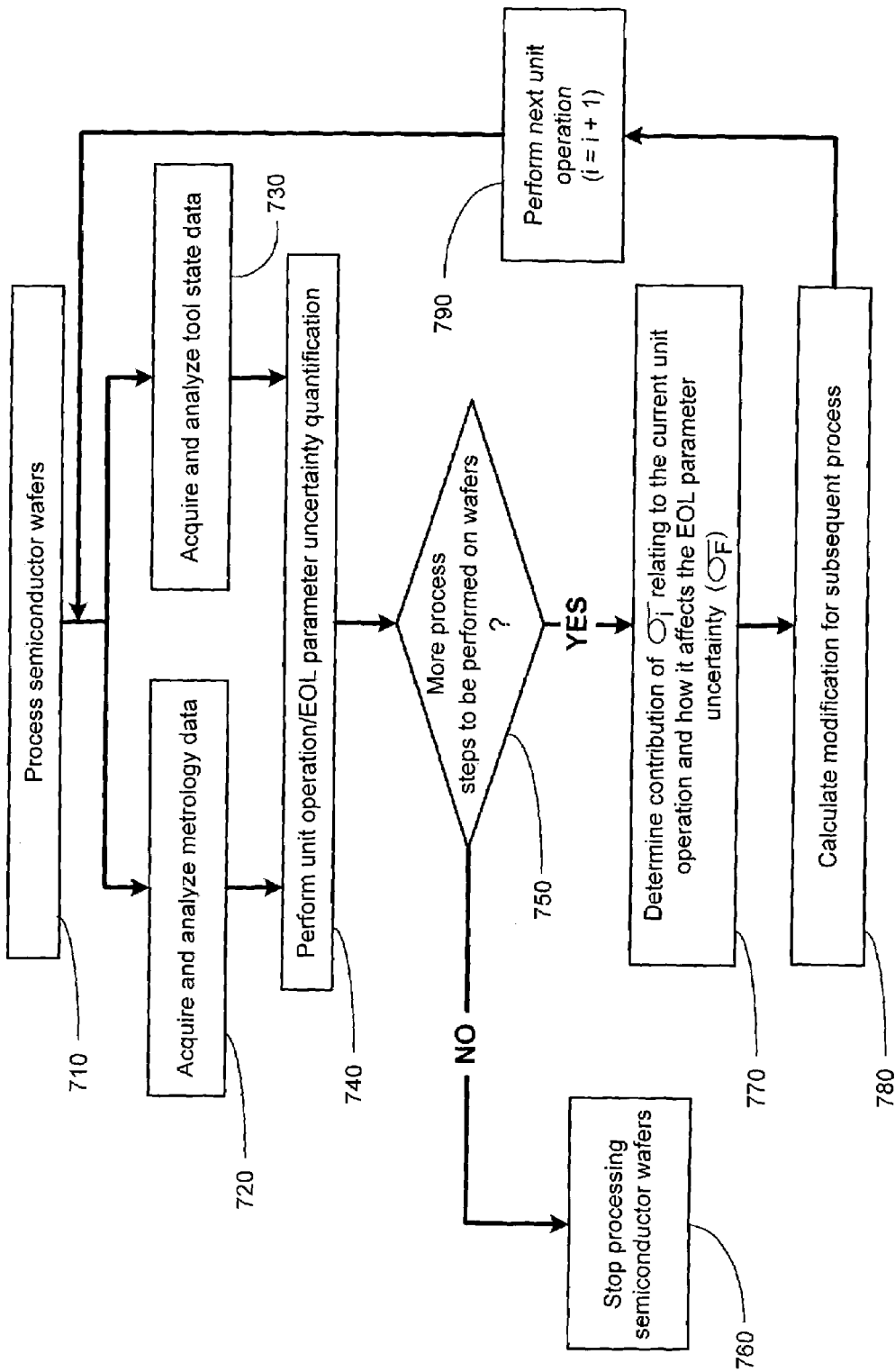
FIG. 7 illustrates a flowchart depiction of a method in accordance with one illustrative embodiment of the present invention.

Turning now to FIG. 7, a flow chart depicting a method in accordance with embodiments of the present invention is illustrated. The system 300 may process semiconductor wafers 105, in one embodiment, from a batch (block 710). Upon processing of the wafers 105, the system 300 may acquire and analyze metrology data relating to the processed semiconductor wafers 105 (block 720). The system 300 may also acquire and analyze tool state data from the tool operations used to process the semiconductor wafers 105 (block 730). Utilizing the metrology data and/or the tool state data, the system 300 may perform an uncertainty quantification process (block 740). This quantification process includes determining uncertainty factors ($\sigma_1, \sigma_2 \ldots \sigma_N$) relating to the unit operations performed on the wafers 105 and using such factors to determine EOL uncertainty factors ($\sigma_F$) relating to certain EOL parameters. A more detailed description of the step of performing the unit operation/EOL uncertainty quantification process is illustrated in FIG. 8 and accompanying description below.

The system 300 may determine whether there are additional processes to be performed on the wafers 105 (block 750). Upon a determination that no additional processes must be performed on the wafers 105, the system 300 stops processing the wafers 105 (block 760). When the system 300 determines that there are additional processes to be performed, the system 300 determines the contribution of the uncertainty factor ($\sigma_i$) of the current unit operation and its affect upon the EOL uncertainty factor ($\sigma_F$) (block 770). In other words, the uncertainty factor relating to the current operation is analyzed to see how it may trickle down to the other processes and how it may affect the EOL uncertainty factor ($\sigma_F$). Based upon this determination, the system 300 may calculate modifications that may be made to subsequent processes based upon the uncertainty factors and/or other manufacturing data (block 780). Based upon the calculated modifications, the system 300 may perform the next unit operation (block 790). Therefore, the integer i of $\sigma_i$ is incremented by 1 (i=i+1). The acquisition of metrology data and the uncertainty quantification processes described above are repeated for the subsequent process performed on the semiconductor wafers 105. These processes are repeated until no more processes remain to be performed on the wafers 105.

Figure 8:
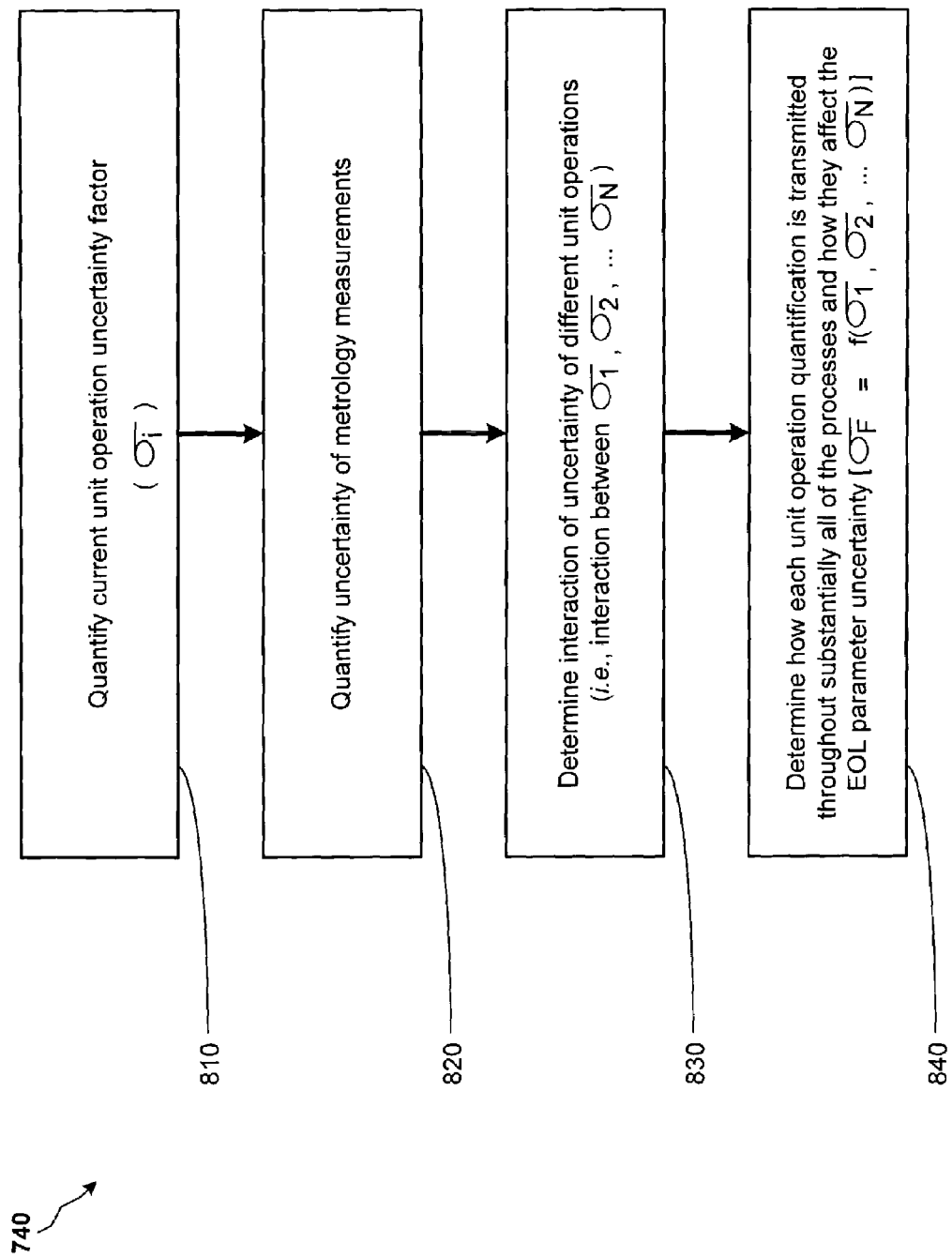
FIG. 8 illustrates a more detailed flowchart depiction of a method of performing a unit operation/EOL parameter uncertainty quantification process of FIG. 6, in accordance with one illustrative embodiment of the present invention.

Turning now to FIG. 8, a more detailed flow chart depicting the unit operation/EOL uncertainty quantification process is illustrated. The system 300 may quantify the current operation uncertainty factor ($\sigma_i$) based upon the metrology and/or the tool state data (block 810). The quantification of the uncertainty factor may include analyzing one or more aspects of the processing of the wafer 105 for this particular process, data relating to the processing tool 610, historical data stored in the database unit 340, and/or the like, in order to determine the uncertainty of the accuracy of the process operation. The system 300 may also quantify an uncertainty factor relating to the metrology measurements, which may include the uncertainty relating to the accuracy of the metrology tool, wafer characteristics, and the like (block 820).

The system 300 may then determine an interaction of the uncertainty factors relating to different unit operations ($\sigma_1, \sigma_2, \sigma_3 \ldots \sigma_N$), which may provide an indication of how particular uncertainty effects are trickled through a series of process operations (block 830). The system 300 then determines how the quantification of the uncertainty relating to each unit operation is transmitted throughout the processes and how they affect the EOL parameter (i.e., calculating $\sigma_F$, which may be a function of $\sigma_1, \sigma_2, \sigma_3 \ldots \sigma_i \ldots \sigma_N$, see Equation 1) (block 840). The completion of the steps described in FIG. 8 substantially completes the process of performing the unit operation/EOL uncertainty quantification process.

Utilizing embodiments of the present invention, the uncertainty of several points in a manufacturing system, such as several unit operations, metrology measurements, and the like, may be quantified. Using this quantification, one or more EOL uncertainty factors may be quantified. When the uncertainty of various components of a manufacturing system is quantified, an analysis of how the uncertainties are transmitted throughout the manufacturing system may be evaluated and process adjustments may be made based upon such uncertainties. Several unit operation uncertainty factors may be used in a function to define an EOL uncertainty, which may provide data to the manufacturing model 640 for more accurately predicting and controlling process operations performed on semiconductor wafers 105. The teachings provided by embodiments of the present invention may be utilized in a variety of manufacturing areas.

The principles taught by the present invention can be implemented in an Advanced Process Control (APC) Framework, such as a Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI. The APC framework is a preferred platform from which to implement the control strategy taught by the present invention. In some embodiments, the APC framework can be a factory-wide software system; therefore, the control strategies taught by the present invention can be applied to virtually any of the semiconductor manufacturing tools on the factory floor. The APC framework also allows for remote access and monitoring of the process performance. Furthermore, by utilizing the APC framework, data storage can be more convenient, more flexible, and less expensive than local drives. The APC framework allows for more sophisticated types of control because it provides a significant amount of flexibility in writing the necessary software code.

Deployment of the control strategy taught by the present invention onto the APC framework could require a number of software components. In addition to components within the APC framework, a computer script is written for each of the semiconductor manufacturing tools involved in the control system. When a semiconductor manufacturing tool in the control system is started in the semiconductor manufacturing fab, it generally calls upon a script to initiate the action that is required by the process controller, such as the overlay controller. The control methods are generally defined and performed in these scripts. The development of these scripts can comprise a significant portion of the development of a control system. The principles taught by the present invention can be implemented into other types of manufacturing frameworks.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. A method, comprising:
    performing a first processing step upon a workpiece;
    determining a first uncertainty factor associated with said first processing step;
    determining a final uncertainty factor associated with an end-of-line parameter relating to said workpiece based upon said first uncertainty factor; and
    performing a process control function based upon said final uncertainty factor.

2. The method of claim 1, wherein processing said workpiece further comprises processing a semiconductor wafer.

3. The method of claim 1, wherein determining said first uncertainty factor associated with said processing step further comprises determining an uncertainty relating to an accuracy of the processing step.

4. The method of claim 1, further comprising acquiring metrology data for determining said first uncertainty factor.

5. The method of claim 1, wherein determining said final uncertainty factor further comprises determining an uncertainty relating to said metrology data.

6. The method of claim 1, further comprising acquiring tool state data for determining said first uncertainty factor.

7. The method of claim 1, wherein acquiring tool state data further comprises acquiring at least one of a pressure data, temperature data, humidity data, and a current data.

8. The method of claim 1, further comprising:
    performing a second processing step upon said workpiece;
    determining a second uncertainty factor associated with said second processing step; and
    determining said final uncertainty factor associated with said end-of-line parameter relating to said workpiece based upon said first and second uncertainty factors.

9. The method of claim 8, wherein determining said final uncertainty factor further comprises using said first and second uncertainty factors in a function to calculate said final uncertainty factor.

10. The method of claim 8, wherein determining said first uncertainty factor further comprises determining whether said first uncertainty factor affects said second uncertainty factor.

11. The method of claim 1, wherein determining a final uncertainty factor further comprises determining an uncertainty factor relating to a drive current parameter, a saturation current parameter, a break-through voltage parameter, a ring oscillation parameter, and a device operation parameter.

12. A method, comprising:
    performing a first processing step upon a workpiece;
    determining a first uncertainty factor associated with said first processing step;
    performing a second processing step upon said workpiece;
    determining a second uncertainty factor associated with said second processing step;
    determining a final uncertainty factor associated with an end-of-line parameter relating to said workpiece based upon said first and second uncertainty factors; and
    performing a process control function based upon said final uncertainty factor.

13. An apparatus, comprising:
    means for performing a first processing step upon a workpiece;
    means for determining a first uncertainty factor associated with said first processing step;
    means for determining a final uncertainty factor associated with an end-of-line parameter relating to said workpiece based upon said first uncertainty factor; and
    means for performing a process control function based upon said final uncertainty factor.

14. A system, comprising:
    a first processing tool to perform a first process upon a workpiece;
    a second processing tool to perform a second process upon said workpiece;
    a controller operatively coupled to said first and second processing tools, said controller for determining a first uncertainty factor associated with said first processing step, determining a second uncertainty factor associated with said second processing step, determining a final uncertainty factor associated with an end-of-line parameter relating to said workpiece based upon said first and second uncertainty factors, and performing a process control function based upon said final uncertainty factor.

15. The system of claim 14, wherein said workpiece is a semiconductor wafer.

16. The system of claim 14, further comprising:
    a tool state data acquisition unit operatively coupled to said process controller and to said first and second processing tools, said tool state data acquisition unit to acquire tool state data relating to operations performed by said first and second processing tools;
    a metrology tool operatively coupled to said process controller and to said first and second processing tools, said metrology tool to acquire metrology data relating to said workpiece;
    a database unit to store said at least one of metrology data and said tool state data;
    a unit operation uncertainty unit to determine at least one of said first and second uncertainty factors; and
    an end-of-line parameter uncertainty unit to calculate said final uncertainty factor.

17. The system of claim 16, wherein said tool state data acquisition unit comprises at least one of a pressure sensor, gas flow sensor, temperature sensor, humidity sensor, and an electrical sensor.

18. An apparatus, comprising:
    a controller adapted to determine a first uncertainty factor associated with a first processing step performed on a workpiece, determine a second uncertainty factor associated with a second processing step performed on said workpiece, determine a final uncertainty factor associated with an end-of-line parameter relating to said workpiece based upon said first and second uncertainty factors, and performing a process control function based upon said final uncertainty factor.

19. The apparatus of claim 18, wherein said workpiece is a semiconductor wafer.

20. The apparatus of claim 18, further comprising:
    a tool state data acquisition unit operatively coupled to said process controller and to said first and second processing tools, said tool state data acquisition unit to acquire tool state data relating to operations performed by said first and second processing tools;
    a metrology tool operatively coupled to said process controller and to said first and second processing tools, said metrology tool to acquire metrology data relating to said workpiece;
    a database unit to store said at least one of metrology data and said tool state data;

a unit operation uncertainty unit to determine at least one of said first and second uncertainty factors; and an end-of-line parameter uncertainty unit to calculate said final uncertainty factor.

21. The apparatus of claim 20, wherein said tool state data acquisition unit comprises at least one of a pressure sensor, gas flow sensor, temperature sensor, humidity sensor, and an electrical sensor.

22. A computer readable program storage device encoded with instructions that, when executed by a computer, performs a method, comprising:

performing a first processing step upon a workpiece;

determining a first uncertainty factor associated with said first processing step;

determining a final uncertainty factor associated with an end-of-line parameter relating to said workpiece based upon said first uncertainty factor; and performing a process control function based upon said final uncertainty factor.

23. The computer readable program storage device encoded with instructions that, when executed by a computer, performs the method of claim 22, wherein processing said workpiece further comprises processing a semiconductor wafer.

24. The computer readable program storage device encoded with instructions that, when executed by a computer, performs the method of claim 22, wherein determining said first uncertainty factor associated with said processing step further comprises determining an uncertainty relating to an accuracy of the processing step.

25. The computer readable program storage device encoded with instructions that, when executed by a computer, performs the method of claim 22, further comprising acquiring metrology data for determining said first uncertainty factor.

26. The computer readable program storage device encoded with instructions that, when executed by a computer, performs the method of claim 22, wherein determining said final uncertainty factor further comprises determining an uncertainty relating to said metrology data.

27. The computer readable program storage device encoded with instructions that, when executed by a computer, performs the method of claim 22, further comprising acquiring tool state data for determining said first uncertainty factor.

28. The computer readable program storage device encoded with instructions that, when executed by a computer, performs the method of claim 22, wherein acquiring tool state data further comprises acquiring at least one of a pressure data, temperature data, humidity data, and a current data.

29. The computer readable program storage device encoded with instructions that, when executed by a computer, performs the method of claim 22, further comprising:

performing a second processing step upon said workpiece;

determining a second uncertainty factor associated with said second processing step; and determining said final uncertainty factor associated with said end-of-line parameter relating to said workpiece based upon said first and second uncertainty factors.

30. The computer readable program storage device encoded with instructions that, when executed by a computer, performs the method of claim 29, wherein determining said final uncertainty factor further comprises using said first and second uncertainty factor in a function to calculate said final uncertainty factor.

31. The computer readable program storage device encoded with instructions that, when executed by a computer, performs the method of claim 29, wherein determining said first uncertainty factor further comprises determining whether said first uncertainty factor affects said second uncertainty factor.

32. The computer readable program storage device encoded with instructions that, when executed by a computer, performs the method of claim 22, wherein determining a final uncertainty factor further comprises determining an uncertainty factor relating to a drive current parameter, a saturation current parameter, a break-through voltage parameter, a ring oscillation parameter, and a device operation parameter.

33. The method of claim 1, further comprising processing a subsequent workpiece.

* * * * *